United States Patent
Gonze et al.

(10) Patent No.: US 8,650,857 B2
(45) Date of Patent: Feb. 18, 2014

(54) APPARATUS AND METHOD FOR ONBOARD PERFORMANCE MONITORING OF EXHAUST GAS PARTICULATE FILTER

(75) Inventors: Eugene V Gonze, Pinckney, MI (US); Kevin W Kirby, Calabasas Hills, CA (US); Amanda Phelps, Malibu, CA (US); Daniel J Gregoire, Thousand Oaks, CA (US)

(73) Assignee: GM Global Technology Operations LLC, Detroit, MI (US)

( * ) Notice: Subject to any disclaimer, the term of this patent is extended or adjusted under 35 U.S.C. 154(b) by 550 days.

(21) Appl. No.: 12/354,837

(22) Filed: Jan. 16, 2009

(65) Prior Publication Data

US 2010/0180577 A1    Jul. 22, 2010

(51) Int. Cl.
*F01N 3/00* (2006.01)
*F01N 3/02* (2006.01)

(52) U.S. Cl.
USPC .............. 60/276; 60/274; 60/275; 60/297; 60/311

(58) Field of Classification Search
USPC ...................... 60/274–276, 297, 311
See application file for complete search history.

(56) References Cited

U.S. PATENT DOCUMENTS

| | | |
|---|---|---|
| 4,276,071 A | 6/1981 | Outland |
| 4,477,771 A | 10/1984 | Nagy et al. |
| 5,492,679 A | 2/1996 | Ament et al. |
| 5,497,099 A * | 3/1996 | Walton .................. 324/641 |
| 6,709,489 B2 * | 3/2004 | Ament et al. ............. 55/282.3 |
| 7,017,338 B2 | 3/2006 | van Nieuwstadt |
| 7,229,597 B2 | 6/2007 | Patchett et al. |
| 7,253,641 B2 * | 8/2007 | Knitt et al. ............... 324/639 |
| 7,260,930 B2 | 8/2007 | Decou et al. |
| 7,303,603 B2 | 12/2007 | Gregoire et al. |
| 7,679,374 B2 * | 3/2010 | Bromberg et al. ........... 324/637 |
| 2007/0163233 A1 | 7/2007 | Cheng |

FOREIGN PATENT DOCUMENTS

DE    102006019783 A1    10/2007

OTHER PUBLICATIONS

Office Action issued in corresponding German Application No. DE102010004513.6 on Apr. 26, 2012; 7 pages.

* cited by examiner

*Primary Examiner* — Thomas Denion
*Assistant Examiner* — Diem Tran
(74) *Attorney, Agent, or Firm* — Cantor Colburn LLP

(57) ABSTRACT

The present invention is directed to a gas particulate treatment system and may include a gas filter and a gas filter performance monitor downstream of the gas filter. The gas filter performance monitor includes a particulate trap operable to collect particulates passing through the gas filter, and a sensing apparatus associated with the gas filter performance monitor that operates to sense particulate collection in the gas filter performance monitor.

12 Claims, 3 Drawing Sheets

APPARATUS AND METHOD FOR ONBOARD PERFORMANCE MONITORING OF EXHAUST GAS PARTICULATE FILTER

FIELD OF THE INVENTION

Exemplary embodiments of the present invention are related to a system for accumulation of soot particulates from the exhaust system of an internal combustion engine and, more specifically, to an apparatus and method for monitoring the performance of the system.

BACKGROUND

Considerable interest has been focused on the reduction of regulated exhaust constituents from internal combustion engines. Recently, focus has been on engines that emit high levels of exhaust particulates with particular attention paid to diesel engines. Diesel engine exhaust is a heterogeneous mixture containing not only gaseous emissions such as carbon monoxide ("CO"), unburned hydrocarbons ("HC") and oxides of nitrogen ("NOX"), but also condensed phase materials (liquids and solids) which constitute particulate matter. Catalyst compositions, and substrates on which the catalysts are disposed, may be provided in diesel engine exhaust systems to convert certain, or all of these exhaust constituents to non-regulated components. For example, diesel exhaust systems may include one or more of a diesel oxidation catalyst, a diesel particulate filter and a catalyst for the reduction of $NO_x$.

One aftertreatment technology in use for particulate matter reduction is the particulate exhaust filter commonly referred to as a diesel particulate filter ("DPF"). There are several known filter structures that are effective in removing the particulate matter from engine exhaust such as honeycomb, wall flow filters, wound or packed fiber filters, open cell foams, sintered metal fibers, etc. The ceramic wall flow monoliths have experienced significant acceptance in high particulate automotive exhaust applications. The filters are structures for physically removing particulate matter from the exhaust and, as such, accumulating particulates relies on the continuing integrity of the filter media. DPF's, especially those constructed of ceramic material may be brittle and can form cracks or other types of failure during normal operation, or during regeneration cycles when the accumulated soot is intentionally combusted at high temperatures to clean the filter and manage exhaust back pressure. Current legislation demands on-board detection of a failed DPF, defined as 90 mg of soot passing through the filter between regenerations. This standard will be raised in the next regulatory tier to 40 mg of soot with the final regulatory tier requiring detection of 17.5 mg of soot between regenerations.

A leading method for on-board detection of a failed DPF relies on the use of individual pressure sensors positioned both upstream and downstream of the filter. Under certain conditions of exhaust flow and soot content in the DPF, the pressure drop across an uncompromised filter has an assumed value. When the filter is compromised from a crack or other failure (ex. melting), the pressure drop will theoretically change thereby providing an indirect method for determining that soot is passing through the system rather than being filtered out. The method does not directly measure the quantity of soot passing through the filter but rather infers its presence in the DPF based on a pressure measurement. Another drawback to this system is that detection can only be performed when certain exhaust flow and soot level conditions in the DPF are met, usually immediately after a regeneration event when no soot is in the DPF. As a result the method does not provide for continuous monitoring of the integrity of the filtration system. Even under ideal conditions, the sensitivity of the system is limited due to the small pressure differential caused by a crack in the DPF. Accordingly it is desirable to provide a system and method of continuous measurement, independent of conditions, having an improved level of robustness over the current method.

SUMMARY OF THE INVENTION

In one exemplary embodiment of the present invention, a gas particulate treatment system includes a gas filter, a gas filter performance monitor downstream of the gas filter having a particulate trap operable to collect particulates passing through the gas filter, and a sensing apparatus associated with the gas filter performance monitor that operates to sense particulate collection in the gas filter performance monitor.

In another exemplary embodiment of the present invention, a method for determining performance of an exhaust particulate filter for an internal combustion engine is disclosed. The method may include the steps of disposing a gas filter performance monitor downstream of an exhaust particulate filter having a particulate trap operable to collect particulates passing through the exhaust particulate filter. Locating a sensing apparatus within the gas filter performance monitor and operating the sensing apparatus to sense particulate collection in the gas filter performance monitor.

BRIEF DESCRIPTION OF THE DRAWINGS

Other objects, features, advantages and details appear, by way of example only, in the following detailed description of embodiments, the detailed description referring to the drawings in which.

DESCRIPTION OF THE EMBODIMENTS

Figure 1:
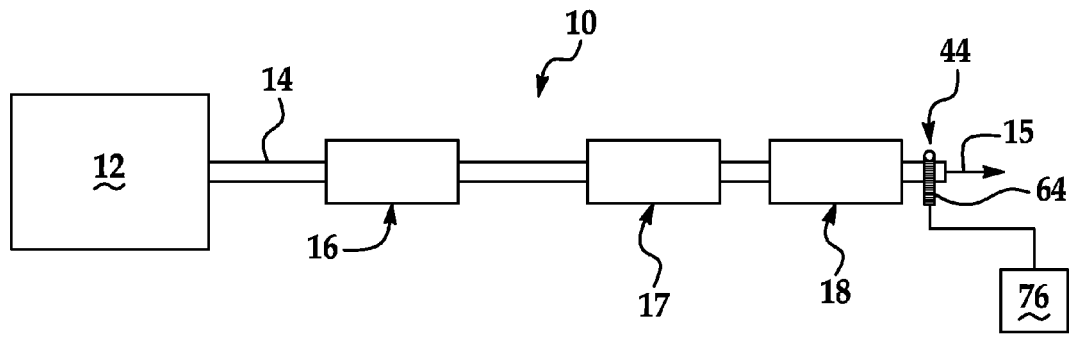
FIG. 1 is a schematic layout of an exhaust treatment system associated with an internal combustion engine.

Referring to FIG. 1, an exemplary embodiment of the present invention is directed to an exhaust treatment system 10 for the reduction of regulated exhaust gas constituents of an internal combustion engine, such as diesel engine 12. The exhaust treatment system 10 includes an exhaust conduit 14 that collects and transports the exhaust gas 15 from the diesel engine 12 to and from the various exhaust treatment components of the exhaust treatment system. The exhaust components may include one or more of an oxidation catalyst 16 that is useful in treating unburned gaseous and non-volatile hydrocarbons and carbon monoxide that are combusted to form carbon dioxide and water. A selective catalytic reduction device ("SCR") 17, which may utilize an ammonia precursor, may be utilized to reduce the oxides of nitrogen ("$NO_x$") resident in the exhaust gas stream. Finally, an exhaust gas filter, commonly referred to as a diesel particulate filter ("DPF") 18, operates to filter the exhaust gas 15 to remove carbon and other particulates therefrom. The sequential ordering of the above-described components has been for descriptive purposes only. The actual ordering in the exhaust treatment system 10 may vary depending upon application and other determining factors.

Figure 2:
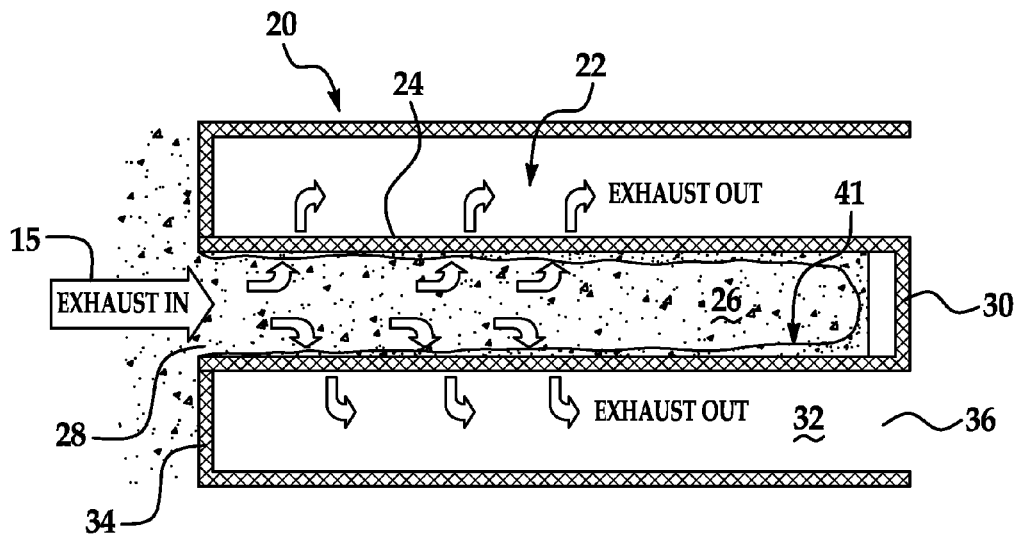
FIG. 2 is a schematic view of a exhaust gas filter associated with the exhaust treatment system of FIG. 1.
Figure 3:
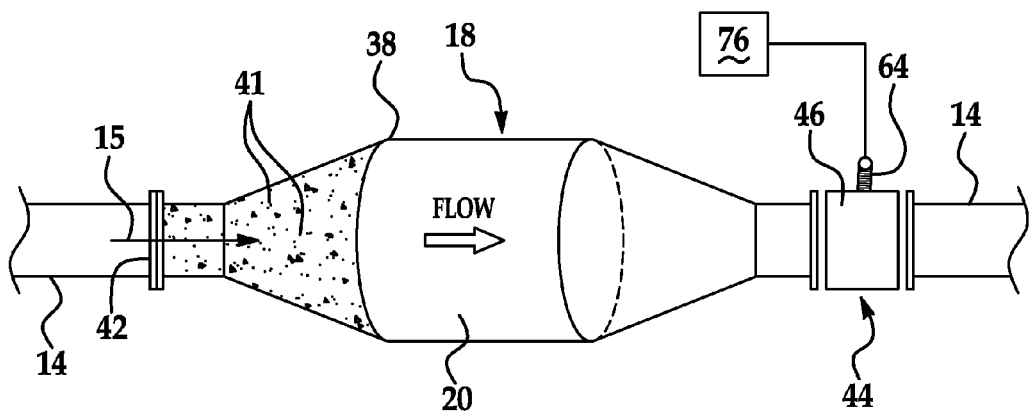
FIG. 3 is a view, in phantom, of a portion of the exhaust treatment system of FIG. 1.

The DPF 18 may be constructed with a ceramic wall flow monolith filter media, wound or packed fiber filters, open cell foams, sintered metal fibers, or other media such as soot bags when used in non-vehicular applications, that are suitable for effective particulate filtration. It is contemplated, and should be understood that any of the filters types described may be used in a DPF 18 without straying from the scope of the invention. For purposes of description, only the ceramic wall flow monolith filter media 20 will be described presently. The ceramic wall flow monolith filter media 20, FIG. 2, includes a plurality of longitudinally extending passages 22 defined by longitudinally extending, porous ceramic walls 24. The longitudinally extending passages 22 include a subset of inlet passages 26 that have an open inlet end 28 and a closed outlet end 30, and a subset of outlet passages 32 that have a closed inlet end 34 and an open outlet end 36. The ceramic wall flow monolith filter media 20 is mounted in a metallic housing or can 38, FIG. 3, and may be supported within the can by a support member of flexible mat (not shown), that is configured not only to support the filter media but to cushion it from shock which may lead to filter failure.

Figure 4:
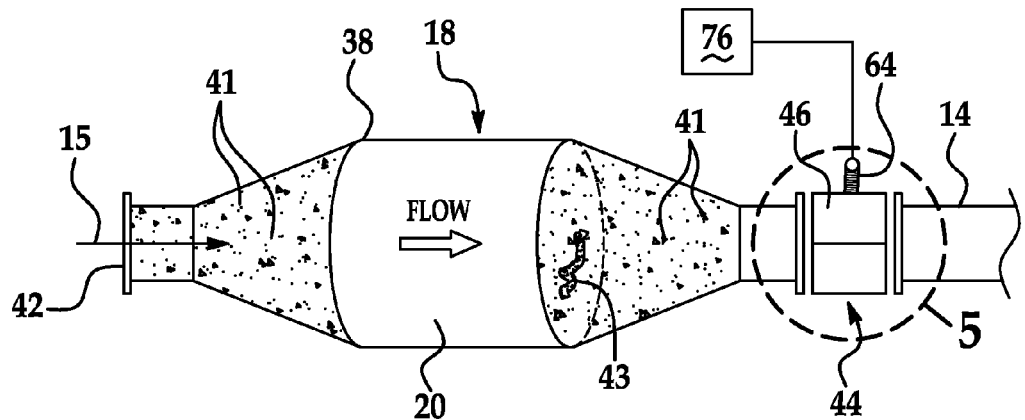
FIG. 4 is a view, in phantom, of a portion of the exhaust treatment system of FIG. 1.

Exhaust gas 15 enters the DPF 18 through housing inlet 42 and enters the inlet passages 26 of the ceramic wall flow monolith filter media 20. The exhaust gas is forced to migrate through the longitudinally extending, porous ceramic walls 24 to the outlet passages 32. It is through this wall flow mechanism that the exhaust gas 15 is filtered of carbon and other particulates 41. It is clear that a crack 43, FIG. 4, in the ceramic wall flow monolith filter media 20 or other failure of the DPF 18 may allow particulate matter 41 to pass through the filter as unfiltered engine exhaust thereby affecting the performance of the exhaust treatment system 10.

Installed within the exhaust conduit 14 at a location downstream of the DPF 18, is an exhaust gas filter performance monitor, referred to as DPF performance monitor 44, FIGS. 3-6. In one exemplary embodiment, the DPF performance monitor includes a small section (relative to the overall volume of the DPF) of ceramic wall flow monolith filter media 46 that preferably includes a plurality of longitudinally extending passages 48 defined by longitudinally extending, porous ceramic walls 50. The longitudinally extending passages 48 include a subset of inlet passages 52 that have an open inlet end 54 and a closed outlet end 56, and a subset of outlet passages 58 that have a closed inlet end 60 and an open outlet end 62. The DPF performance monitor 44 is mounted in or otherwise associated with the exhaust conduit 14 such that as exhaust gas 15 enters it flows through the inlet passages 52 of the ceramic wall flow monolith filter media 46 and is forced to migrate through the longitudinally extending, porous ceramic walls 50 to the outlet passages 58. The ceramic wall flow monolith filter media 46 of the DPF performance monitor operates as a particulate trap. During normal operation of the DPF 18, the exhaust gas 15 passing through the DPF performance monitor 44 should contain little or no particulate matter and, as such, the particulate loading in the particulate trap should remain substantially at or near zero.

Figure 7:
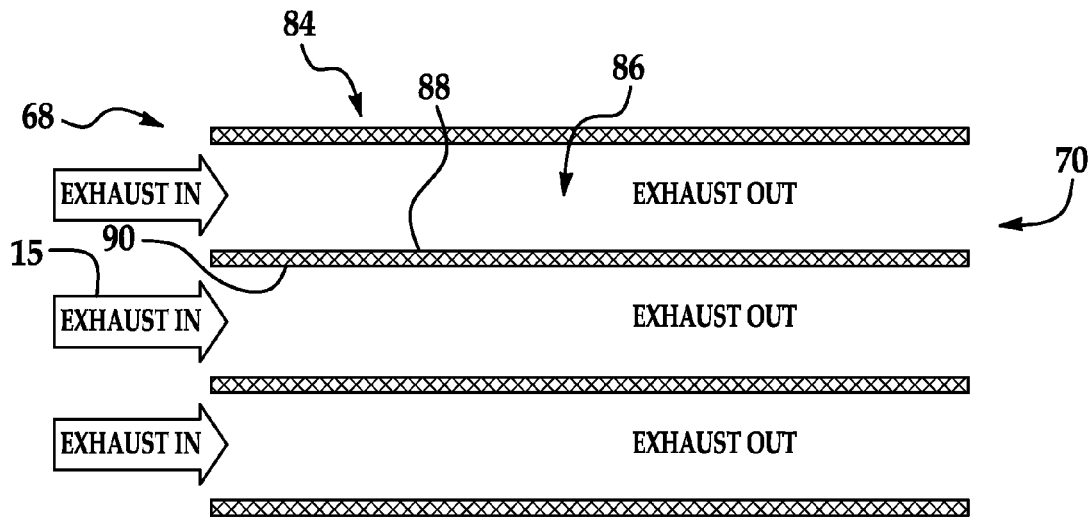
FIG. 7 is a schematic view of an alternate embodiment of the exhaust filter performance monitor particulate trap of FIG. 6.

Another non-limiting embodiment the DPF performance monitor, FIG. 7, includes a small section (relative to the overall volume of the DPF) of ceramic flow through media 84 that preferably includes a plurality of longitudinally extending passages 86 defined by longitudinally extending, ceramic walls 88. A zeolite based coating 90 may be applied to the ceramic walls 88. The zeolite coating operates to adsorb or trap particulate matter from the exhaust gas flowing through the ceramic flow through media 84. In this embodiment, exhaust gas 15 is not required to flow through porous ceramic walls thereby reducing effects of backpressure in the exhaust treatment system 10.

Figure 5:
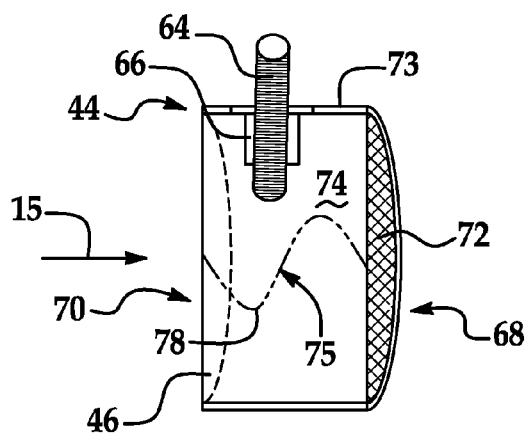
FIG. 5 is an enlarged view of a portion of the exhaust system of FIG. 1, taken at circle 5 of FIG. 4.
Figure 6:
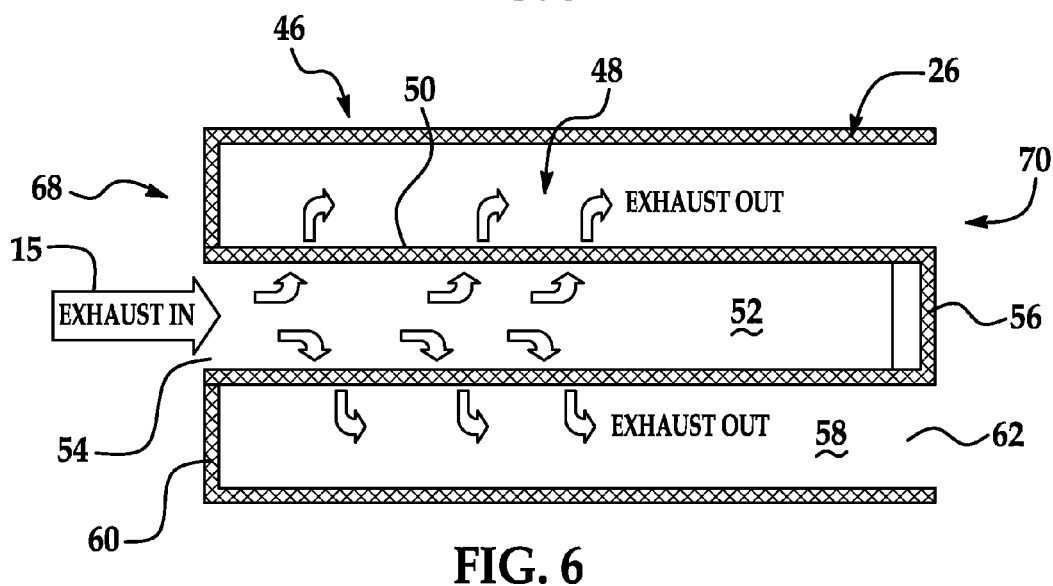
FIG. 6 is a schematic view of a exhaust filter performance monitor particulate trap associated with the exhaust treatment system of FIG. 1.

As shown in detail in FIG. 5, a sensing apparatus such as RF antenna 64 penetrates the wall of DPF performance monitor 44 and extends into the ceramic monolith filter media 46, 84. The RF antenna is sealingly fixed to the DPF performance monitor 44 using sleeve 66 or other suitable device or method that will support the antenna while avoiding leakage of exhaust gas. Upstream and downstream ends, 68 and 70 respectively, of the ceramic monolith filter media 46, 84 of the DPF performance monitor 44 have a reflective metallic coating 72 applied thereto that defines an RF shorting screen at each end of the filter media. In another embodiment of the DPF performance monitor 44, a metallic screen or mesh may be substituted for the metallic coating with similar effect. The metallic conduit 73 and the metallic coating 72 on both ends of the ceramic monolith filter media 46, 84 define a microwave electromagnetic cavity 74 with a specific electromagnetic signature 75. The electromagnetic cavity may be excited by excitation of the RF antenna 64 operating in a first, sending mode. The same RF antenna operating in a second, receiving mode receives the reflection of the microwave in the cavity 74 and provides a corresponding output signal to a controller 76. In another, non-limiting embodiment, the single RF antenna may be replaced by two RF antennas (not shown). The microwave electromagnetic cavity 74 may be excited by excitation of the first RF antenna operating in a first, sending mode. The second RF antenna operating in a second, receiving mode receives the signal provided by the first RF antenna and provides a corresponding output signal to a controller 76.

Figure 8:
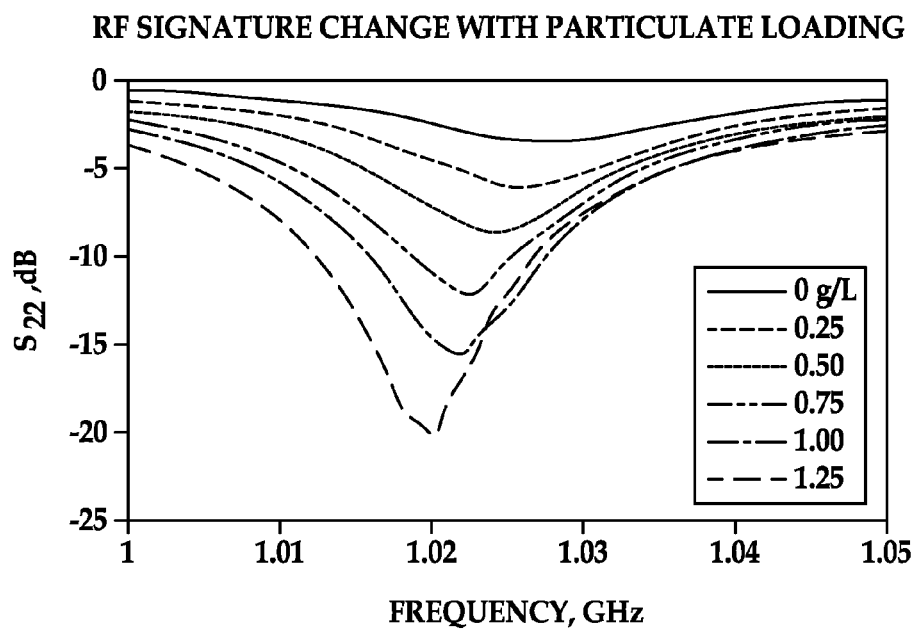
FIG. 8 is a graph illustrating the RF signature change of the exhaust filter performance monitor particulate trap of FIG. 6 with particulate loading.

The electromagnetic signature 75 of the electromagnetic cavity 74 is characterized by a set of absorption lines and resonances, FIG. 8, that are dependent upon the physical geometry, the electrical properties of the material within the cavity and the order of mode excited. While the ceramic monolith filter media 46, 84 is virtually invisible to the RF signal, any soot particles that have collected on the porous ceramic walls 50, 88 will be dispersed sufficiently uniformly throughout the volume of the ceramic monolith filter media 46, 84 so that the filter behaves like an artificial dielectric and its permittivity increases as the soot loading increases. That permittivity or dielectric constant can then be measured by microwave techniques and, in particular, since the dielectric loading of the material within the microwave electromagnetic cavity 74 affects the electromagnetic signature of the cavity, that effect can be used to measure the effective dielectric constant and, as such, the soot content of the DPF performance monitor 44.

Controller 76 associated with the RF antenna 64, or antennas, monitors the electromagnetic signature. In the case of an automotive application the controller may be a vehicle or powertrain controller. The RF antenna 64, or antennas, sends an electromagnetic signal to the microwave electromagnetic cavity 74 and measures the power reflected back from the cavity. The reflected power, measured over a range of frequencies constitutes the cavity signature. The electromagnetic signal is typically in the radio-frequency (RF) regime and most likely within the range of frequency known as microwaves (typically 1 to 100 GHz) however other frequencies and frequency ranges are contemplated. The accumulation of particulates in the ceramic monolith filter media 46, 84 of the DPF performance monitor 44 may alter the RF signature significantly and it is possible to quantify the soot by observing the change in the signature. FIG. 8 shows simulated RF signatures for various soot concentration levels in the DPF performance monitor 44 and how the soot is detected by changes in the signature. In practice, any frequency range may be used as long as it is high enough to be supported within the microwave electromagnetic cavity 74 and as long as it exhibits one or more resonant absorption peaks 78, FIG. 5, that can be used by the controller 76 to determine soot accumulation. As soot is added to the DPF performance monitor 44, the absorption peaks 78 shift to different frequencies because the soot increases the composite permittivity of the ceramic monolith filter media 46, 84 resulting in electrical elongation of the filter media. Upon a determination by the controller 76 that soot accumulation is occurring in the DPF performance monitor 44, the controller 76 may generate a signal notifying the operator that the exhaust treatment system 10 requires service.

While the invention has been described having applicability to a motor vehicle, and in particular to a motor vehicle having a diesel engine, it should be understood that this is a non-limiting embodiment as a DPF performance monitor, of the type herein described, may have applicability with any system in which gas flow is being monitored for particulate presence. The non-limiting, vehicular application of the DPF performance monitor 44 herein described above is just one contemplated application of the invention and it is contemplated that the essence of the invention may be applied to non-diesel vehicular applications as well as non-mobile, stationary applications, for instance, with the same outcome.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the present application.

What is claimed is:

1. A gas particulate treatment system comprising;
a gas filter;
a gas filter performance monitor positioned downstream of the gas filter, the gas filter performance monitor having a particulate trap associated therewith that is configured to collect particulates passing through the gas filter; and
a sensing apparatus positioned within the particulate trap and associated with the gas filter performance monitor configured to sense particulate collection in the particulate trap based on electromagnetic activity in the gas filter performance monitor.

2. The gas particulate treatment system of claim 1, the particulate trap disposed in a microwave electromagnetic cavity.

3. The gas particulate treatment system of claim 2, the sensing apparatus including at least one RF antenna configured to operate in a first mode to emit an RF signal into the microwave electromagnetic cavity and in a second mode to receive a reflection of the RF signal.

4. The gas particulate treatment system of claim 3, the sensing apparatus including a controller configured to compare the RF signal with the reflection of the RF signal to determine particulate loading in the particulate trap.

5. The gas particulate treatment system of claim 4, the controller configured to generate a notification signal indicating particulate loading in the particulate trap.

6. An exhaust gas treatment system for an internal combustion engine comprising;
an exhaust conduit for collecting and transporting exhaust gas from the internal combustion engine;
an exhaust gas filter in fluid communication with the exhaust conduit and operable to remove exhaust gas particulate matter from the exhaust gas;
an exhaust gas filter performance monitor in fluid communication with the exhaust conduit and positioned downstream of the exhaust gas filter for receiving filtered exhaust gas therefrom, the exhaust gas filter performance monitor having a particulate trap located therein through which the filtered exhaust gas flows;
a particulate sensor positioned within the particulate trap configured to sense particulate collection therein based on electromagnetic activity in the exhaust gas performance monitor.

7. The exhaust gas treatment system for an internal combustion engine of claim 6, the particulate trap of the exhaust gas filter monitor comprising a ceramic wall flow monolith filter media having a reflective metallic coating at inlet and outlet ends defining RF shorting screens to define a microwave electromagnetic cavity, having an electromagnetic signature, therebetween.

8. The exhaust gas treatment system for an internal combustion engine of claim 7, the microwave electronic cavity including;
a sensing apparatus in communication therewith and configured, in a first mode to emit an RF signal into the microwave electromagnetic cavity and, in a second mode to receive a reflection of the RF signal; and
a controller configured to compare the RF signal with the reflection of the RF signal to determine particulate loading in the particulate trap.

9. The exhaust gas treatment system for an internal combustion engine of claim 8, the controller configured to generate a notification signal indicating particulate loading in the particulate trap.

10. A method for monitoring the performance of an exhaust gas particulate filter for an internal combustion engine comprising;
disposing a gas filter performance monitor downstream of the exhaust gas particulate filter, the gas filter performance monitor having a particulate trap operable to collect particulates passing through the exhaust gas particulate filter;
disposing a sensing apparatus within the particulate trap of the gas filter performance monitor; and
operating the sensing apparatus to sense particulate collection in the particulate trap of the gas filter performance monitor based on electromagnetic activity in the gas filter performance monitor.

11. The method of determining performance of an exhaust gas particulate filter for an internal combustion engine of claim 10, further comprising the steps of;
locating a reflective metallic coating at inlet and outlet ends of the gas filter performance monitor particulate trap to define RF shorting screens thereon and a microwave electronic cavity therebetween, the microwave electronic cavity having an electromagnetic signature.

12. The method of determining performance of an exhaust gas particulate filter for an internal combustion engine of claim 11, further comprising the steps of;

operating the sensing apparatus in a first mode to emit an RF signal into the microwave electromagnetic cavity and in a second mode to receive a reflection of the RF signal; and comparing the RF signal with the reflection of the RF signal to determine particulate loading in the particulate trap.

\* \* \* \* \*